(12) United States Patent
Varadan et al.

(10) Patent No.: US 10,541,052 B2
(45) Date of Patent: Jan. 21, 2020

(54) RETROACTIVE EXTRACTION OF CLINICALLY RELEVANT INFORMATION FROM PATIENT SEQUENCING DATA FOR CLINICAL DECISION SUPPORT

(71) Applicant: KONINKLIJKE PHILIPS N.V., Eindhoven (NL)

(72) Inventors: Vinay Varadan, New York, NY (US); Sitharthan Kamalakaran, Pelham, NY (US); Angel Janevski, New York, NY (US); Nilanjana Banerjee, Armonk, NY (US); Nevenka Dimitrova, Pelham Manor, NY (US)

(73) Assignee: Koninklijke Philip N.V., Eindhoven (NL)

( * ) Notice: Subject to any disclaimer, the term of this patent is extended or adjusted under 35 U.S.C. 154(b) by 1115 days.

(21) Appl. No.: 14/363,110

(22) PCT Filed: Nov. 29, 2012

(86) PCT No.: PCT/IB2012/056839
§ 371 (c)(1),
(2) Date: Jun. 5, 2014

(87) PCT Pub. No.: WO2013/084121
PCT Pub. Date: Jun. 13, 2013

(65) Prior Publication Data
US 2014/0365243 A1 Dec. 11, 2014

Related U.S. Application Data

(60) Provisional application No. 61/566,919, filed on Dec. 5, 2011.

(30) Foreign Application Priority Data

Dec. 7, 2011 (EP) ................................... 11192475

(51) Int. Cl.
*G16H 50/20* (2018.01)
*G16H 10/60* (2018.01)

(52) U.S. Cl.
CPC ............. *G16H 50/20* (2018.01); *G16H 10/60* (2018.01)

(58) Field of Classification Search
CPC ............................... G06Q 50/22; G06Q 50/24
See application file for complete search history.

(56) References Cited

U.S. PATENT DOCUMENTS

2006/0064247 A1* 3/2006 Yuan ...................... G06Q 50/22
702/19
2007/0088509 A1* 4/2007 Cheng ..................... G06F 19/18
702/20

(Continued)

FOREIGN PATENT DOCUMENTS

| EP | 0962878 A2 | 5/1999 |
| WO | 2005027716 A2 | 3/2005 |
| WO | 2005036446 A2 | 4/2005 |

OTHER PUBLICATIONS

Martino, Robert L., et al. "Parallel Computing in Biomedical Research." Science 265 (1994): p902(7). ProQuest. Web. Sep. 19, 2019. (Year: 1994).*

*Primary Examiner* — Lena Najarian

(57) ABSTRACT

A catalog (34) of molecular marker tests specifies molecular marker tests annotated with clinical applicability annotations. An electronic patient medical record (22) stores genetic sequencing data (20) of a patient. A clinical decision support (CDS) system (30) is configured to track the clinical context of the patient wherein the clinical context includes at least a disease diagnosis and a current patient care stage. A catalog search module (32) is configured to search the catalog of molecular marker tests to identify a molecular marker test having clinical applicability to the patient in the (Continued)

Figure 1:
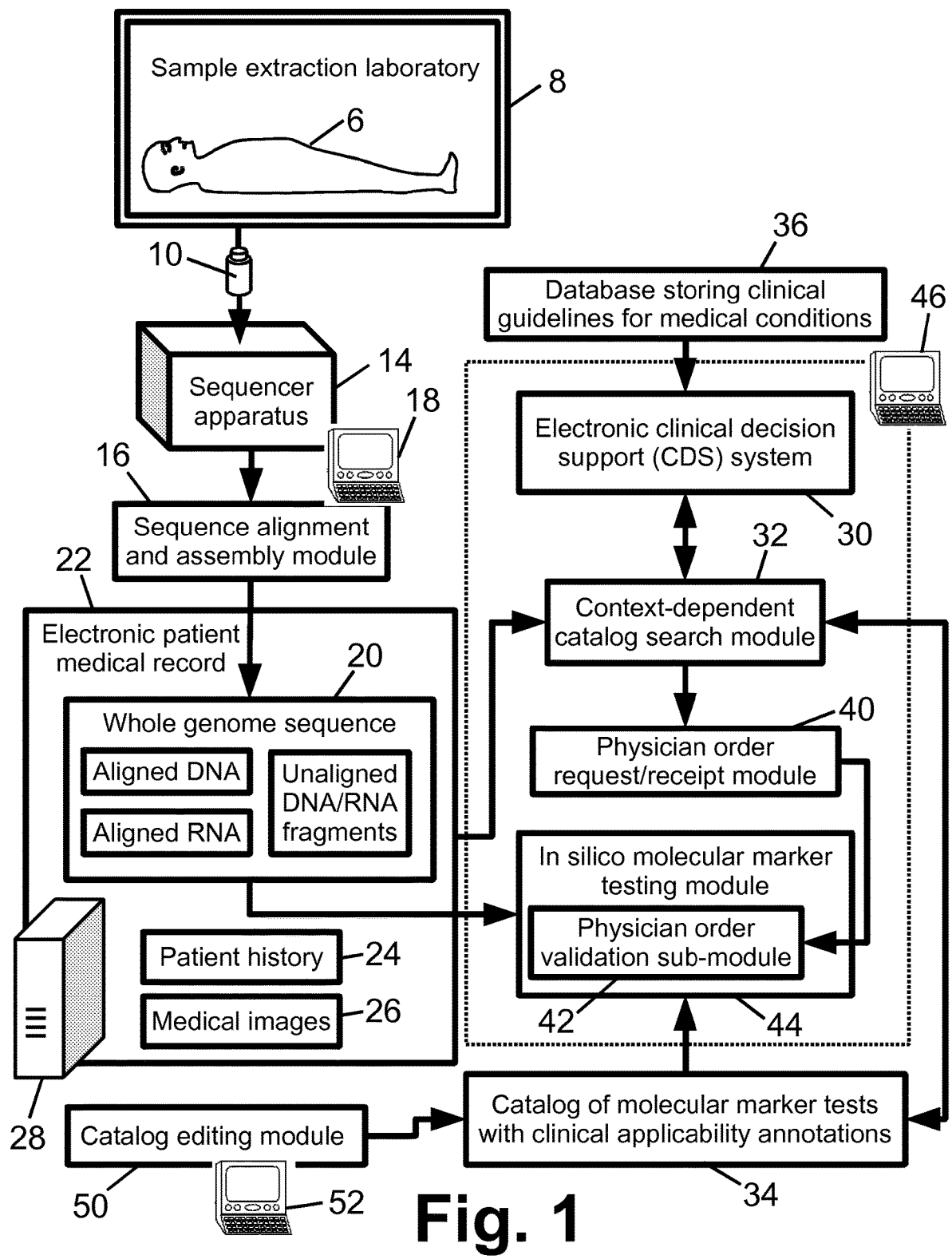

clinical context tracked by the CDS system. The search is automatically triggered by occurrence of a trigger event defined by a set of triggering rules. A testing module (44) is configured to perform a molecular marker test identified by the identification module in silico using the genetic sequencing data of the patient stored in the electronic patient medical record.

12 Claims, 5 Drawing Sheets

(56) References Cited

U.S. PATENT DOCUMENTS

| | | | | |
|---|---|---|---|---|
| 2008/0082503 | A1* | 4/2008 | Jung | G06F 19/18 |
| 2008/0270438 | A1* | 10/2008 | Aronson | G06F 19/322 |
| 2009/0192363 | A1* | 7/2009 | Case | G06F 19/322 |
| | | | | 600/300 |
| 2010/0063839 | A1 | 4/2010 | Alsafadi | |
| 2011/0077964 | A1 | 3/2011 | Janevski et al. | |
| 2011/0301859 | A1 | 12/2011 | Carter et al. | |

\* cited by examiner

RETROACTIVE EXTRACTION OF CLINICALLY RELEVANT INFORMATION FROM PATIENT SEQUENCING DATA FOR CLINICAL DECISION SUPPORT

This application is a national stage application under 35 U.S.C. § 371 of International Application No. PCT/IB2012/056839 filed on Nov. 29, 2012 and published in the English language on Jun. 13, 2013 as International Publication No. WO/2013/084121, which claims priority to U.S. Application No. 61/566,919 filed on Dec. 5, 2011 and EP Application No. 11192475.9 filed on Dec. 7, 2011, the entire disclosures of which are incorporated herein by reference.

The following relates to the medical arts, oncology arts, genomic arts, and related arts.

In a typical breast cancer workflow a suspicious breast lesion is detected and a patient undergoes a biopsy procedure in order to extract a tissue sample of the lesion. The sample undergoes an immunohistology procedure employing suitable staining to assess whether the lesion is malignant. In some clinical settings, DNA staining may be employed to assess the number of tumor cells having multiple chromosomal copies. These tests may be deemed sufficient to order a chemotherapy regimen.

In some clinical settings, the immunohistology may be followed by targeted assessment of the estrogen receptor (ER) molecular marker. If the patient tests positive for a high ER level correlative with estrogen receptor-positive (ER+) breast cancer, then a tamoxifen regimen that targets the estrogen receptor may be ordered. If it is suspected that aggressive treatment may be required, an Oncotype DX® test (available from Genomic Health, Inc., Redwood City, Calif., USA) may be ordered. This test measures the levels of 21 molecular markers that have been clinically validated as being probative of breast cancer. Additionally or alternatively, another advanced breast cancer test such as MammaPrint®, which measures the levels of 70 molecular markers, may be ordered. An aggressive treatment regimen combining chemotherapy and tamoxifen may be ordered based on the results of an Oncotype DX® or MammaPrint® test. Each test requires a sample of the tumor, which may be obtained in a single biopsy, multiple biopsies, or may be obtained from the surgically extracted tumor (if available).

The Oncotype DX® and MammaPrint® tests are commercial molecular marker tests that are validated for clinical use in assessing breast cancer. Additional molecular marker tests are available for breast cancer assessment and for assessment of other medical conditions. Moreover, ongoing clinical research is expected to continually expand the catalog of available molecular marker tests.

The advisability of using a given molecular marker test in a clinical setting (e.g., to diagnose a condition in a medical patient and/or formulate a treatment plan for the patient, to assess likelihood of recurrence of cancer that is in remission, or so forth) can be based on numerous factors, such as the disease diagnosis (if available) and the patient care stage (e.g., diagnosis, prognosis, therapy, remission monitoring, or so forth). Consideration also may be given to the treating physician's opinion of the clinical studies underlying the molecular marker test, as well as various certifications that the test may have received. For example, a certification or validation awarded by the Food and Drug Administration (FDA) in the United States may be persuasive for a U.S. doctor, but may be less persuasive, or unpersuasive, for a doctor based in Europe.

In view of the foregoing, it will be appreciated that different molecular marker tests may become relevant at different times during the treatment of a patient. Each time the physician orders a molecular marker test, a suitable sample (e.g., biopsy sample) is drawn (unless an unused previously acquired sample remains available) and the test is performed by processing the sample. Sample extraction such as a biopsy procedure can be stressful, painful, and inconvenient for the patient with some associated risks of comorbidities resulting from the procedure. Moreover, effective use of molecular marker tests depends upon the physician maintaining up-to-date knowledge of the catalog of available tests. This is difficult since the catalog is constantly changing (usually expanding, although occasionally a test may become obsolete or otherwise "out of favor" and removed). Practicing physicians may not have time to keep current on this information, especially if the physician is not well-versed genomic analysis. On the other hand, research scientists are more likely to have up-to-date knowledge of available molecular marker tests, but tend to be less involved, or uninvolved, with treating specific patients.

As a consequence, the physician may delay or fail entirely to order probative molecular marker tests. This can have adverse consequences for the patient, such as delay or complete omission of a potentially effective treatment that might have been identified by timely testing.

The following contemplates improved apparatuses and methods that overcome the aforementioned limitations and others.

According to one aspect, an apparatus comprises: a catalog of molecular marker tests specifying molecular marker tests annotated with clinical applicability annotations; an electronic patient medical record storing genetic sequencing data of a patient; a clinical decision support (CDS) system configured to track the clinical context of the patient wherein the clinical context includes at least a disease diagnosis and a current patient care stage (and optionally may include other contextual information such as the patient's location in the care cycle, monitored response to therapy, monitoring of side effects of therapy, monitoring and followup to detect local, regional, or distant metastases, and so forth); a catalog search module configured to search the catalog of molecular marker tests to identify a molecular marker test having clinical applicability to the patient in the clinical context tracked by the CDS system wherein the search is automatically triggered by occurrence of a trigger event defined by a set of triggering rules; and a testing module configured to perform a molecular marker test identified by the identification module in silico using the genetic sequencing data of the patient stored in the electronic patient medical record. The CDS system, the catalog search module, and the testing module are suitably embodied by one or more electronic data processing devices.

According to another aspect, a method is operative in conjunction with a catalog of molecular marker tests specifying molecular marker tests annotated with clinical applicability annotations and in conjunction with stored genetic sequencing data of a patient. The method comprises: electronically tracking the clinical context of the patient using a clinical decision support (CDS) system; during the electronic tracking, automatically detecting occurrence of a trigger event defined by a set of triggering rules; automatically triggering an electronic search of the catalog to identify a molecular marker test having clinical applicability to the patient in the clinical context tracked by the CDS system; and performing the identified molecular marker test in silico using the stored genetic sequencing data.

According to another aspect, an apparatus comprises a catalog of molecular marker tests specifying molecular marker tests annotated with clinical applicability annotations, and an electronic data processing device configured to perform a method including: tracking the clinical context of a patient; detecting a change in the clinical context during the tracking that triggers a search of the catalog of molecular marker tests having clinical applicability to the patient in the clinical context.

According to another aspect, an apparatus as set forth in the immediately preceding paragraph further includes an electronic storage storing a whole genome sequence of the patient, and the electronic data processing device is further configured to perform a molecular marker test located by the searching in silico using genetic sequencing data of the patient stored in the electronic storage. In some such embodiments the electronic data processing device is further configured to propose the molecular marker test located by the search triggered by a triggering rule or clinical event to a physician overseeing medical care of the patient and receive a physician order to perform the molecular marker test located by the searching, and the electronic data processing device performs the molecular marker test located by the searching conditional upon and after receiving the physician order.

One advantage resides in integrating timely consideration and performance (when deemed appropriate by the treating physician) of molecular marker tests as part of the overall treatment workflow for a patient.

Another advantage resides in reducing the number of patient tissue or blood samples needed for running multiple molecular marker tests, thus reducing costs and burden to patients.

Another advantage resides in facilitating expedited adoption of newly developed or newly validated or newly certified molecular marker tests.

Another advantage resides in providing an updatable and automatically searchable catalog of molecular marker tests that is automatically searched for relevant molecular marker tests when the clinical context of a patent changes.

Another advantage resides in providing an updatable and automatically and actively searchable catalog of molecular marker tests, in which new searches are automatically triggered by triggering rules pertaining to events such as a change in the patient's status, a change in the clinical decision support system guidelines, or a change in the content of the catalog. The catalog is integrated with a clinical decision support (CDS) system, but the updating of the catalog is independent of the CDS system.

Another advantage resides in providing an updatable and automatically searchable catalog of molecular marker tests that is integrated with a clinical decision support (CDS) but which can be updated by a human curator who does not have a detailed understanding of the CDS system.

Another advantage resides in providing real-time in silico molecular marker testing responsive to the physician ordering a proposed clinically applicable molecular marker test.

Numerous additional advantages and benefits will become apparent to those of ordinary skill in the art upon reading the following detailed description.

The invention may take form in various components and arrangements of components, and in various process operations and arrangements of process operations. The drawings are only for the purpose of illustrating preferred embodiments and are not to be construed as limiting the invention.

FIG. 1 diagrammatically shows a medical system for context-dependent medical marker test identification and administration as disclosed herein.

Figure 2:
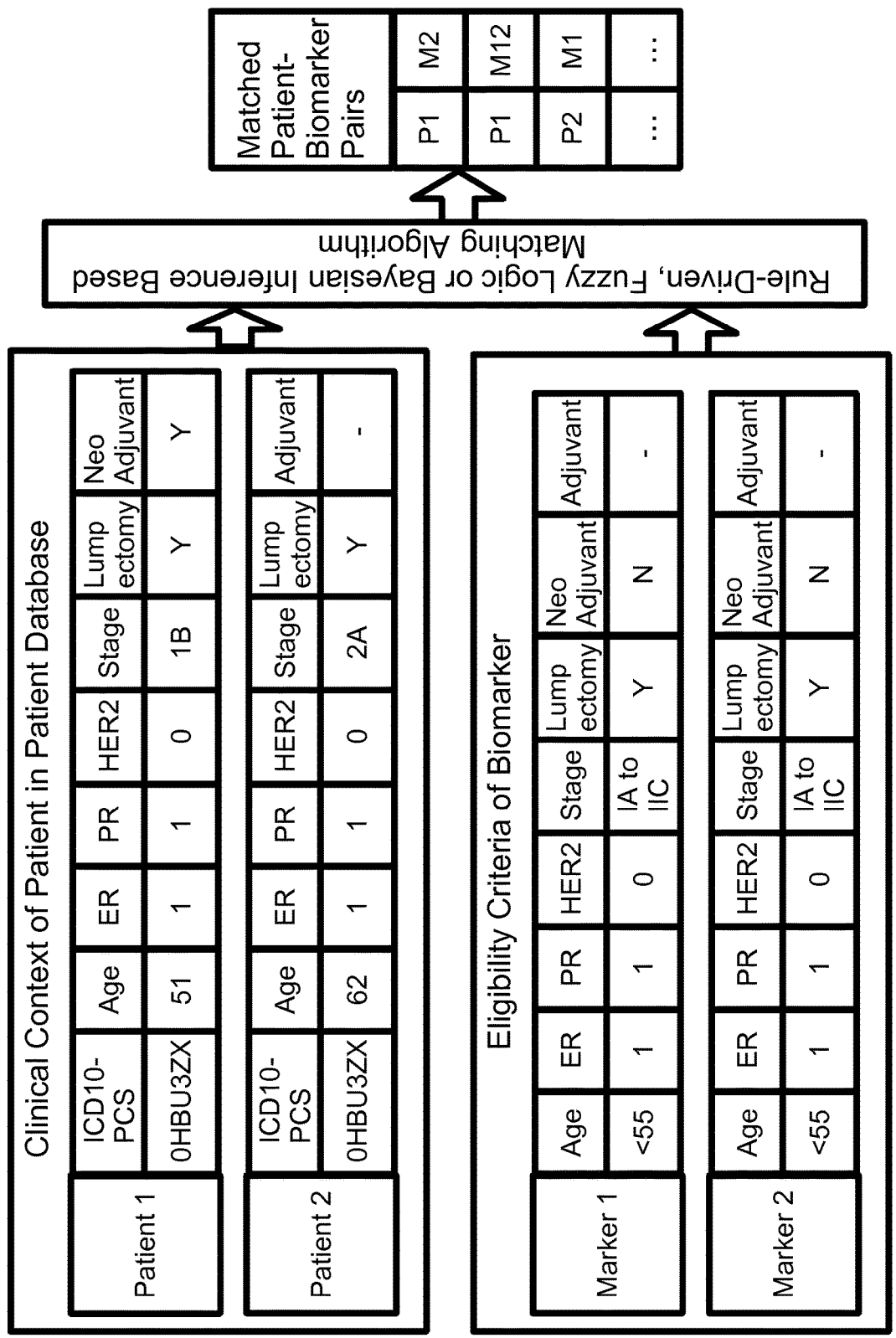

FIG. 2 diagrammatically shows active context-dependent searching of the catalog of molecular marker tests of FIG. 1 to perform context-dependent medical marker test identification.

Figure 3:
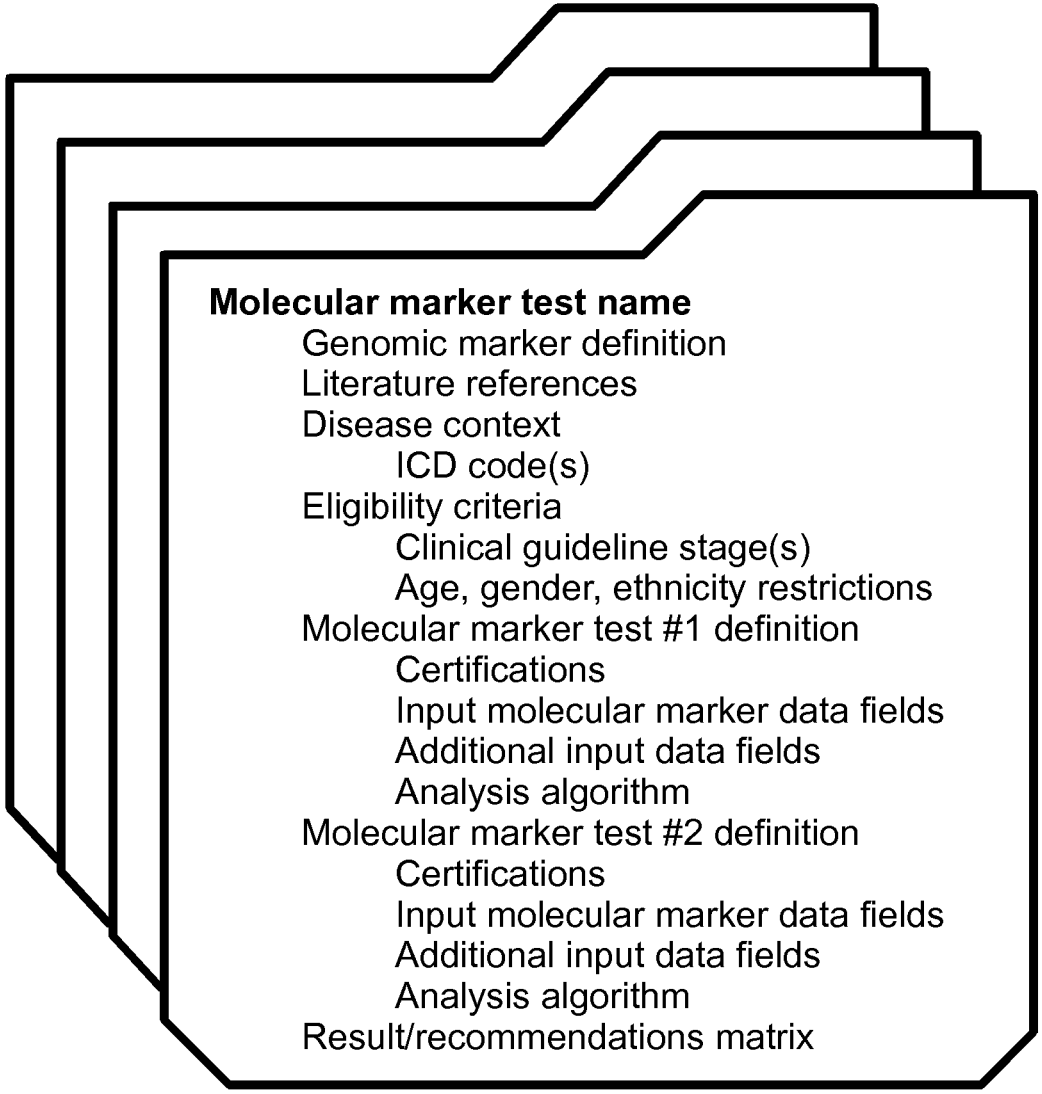

FIG. 3 diagrammatically shows an entry in the database of molecular marker tests that is diagrammatically shown in FIG. 1.

Figure 4:
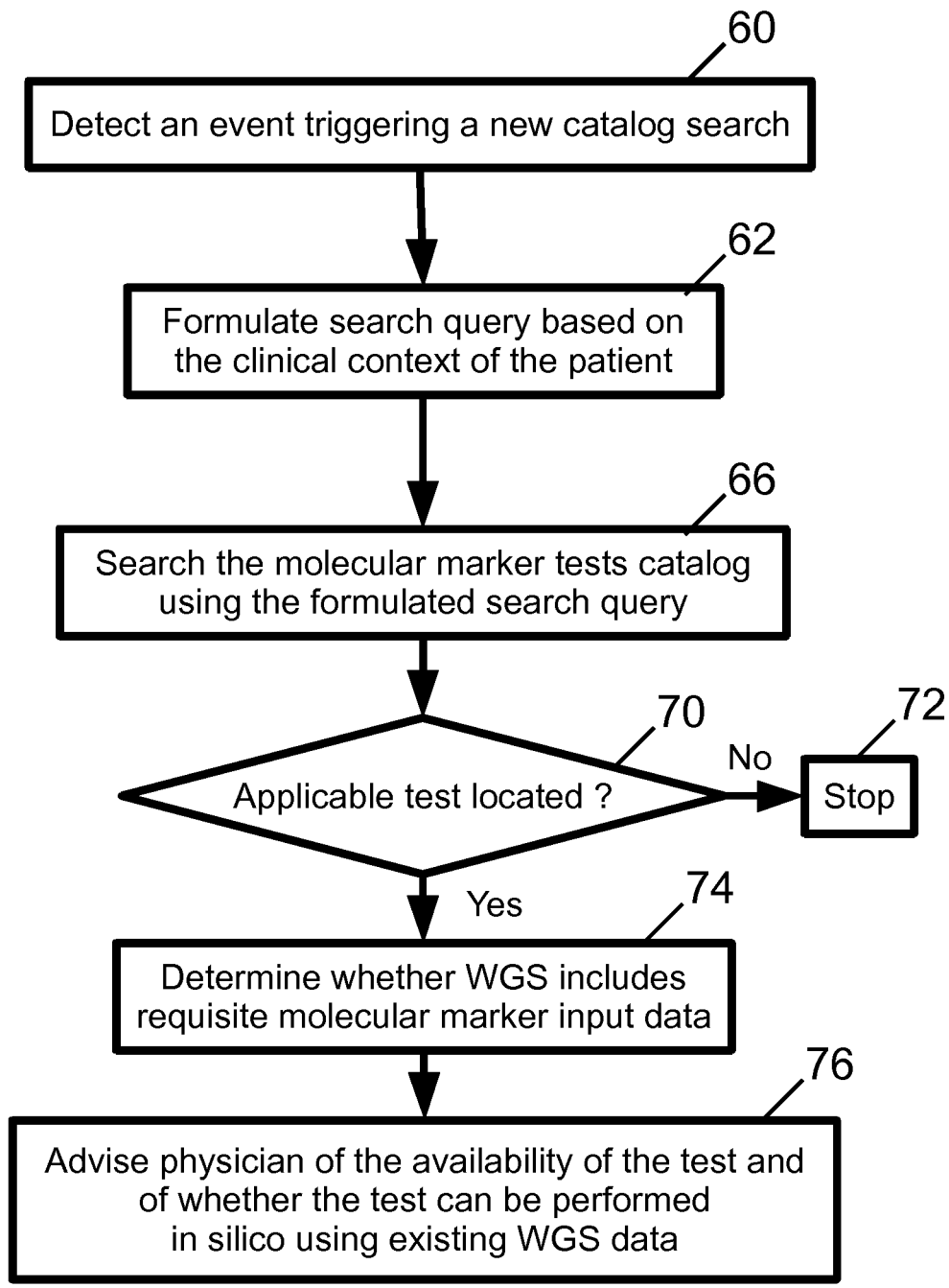

FIG. 4 diagrammatically shows context-dependent medical marker test identification as suitably performed by the system of FIG. 1.

Figure 5:
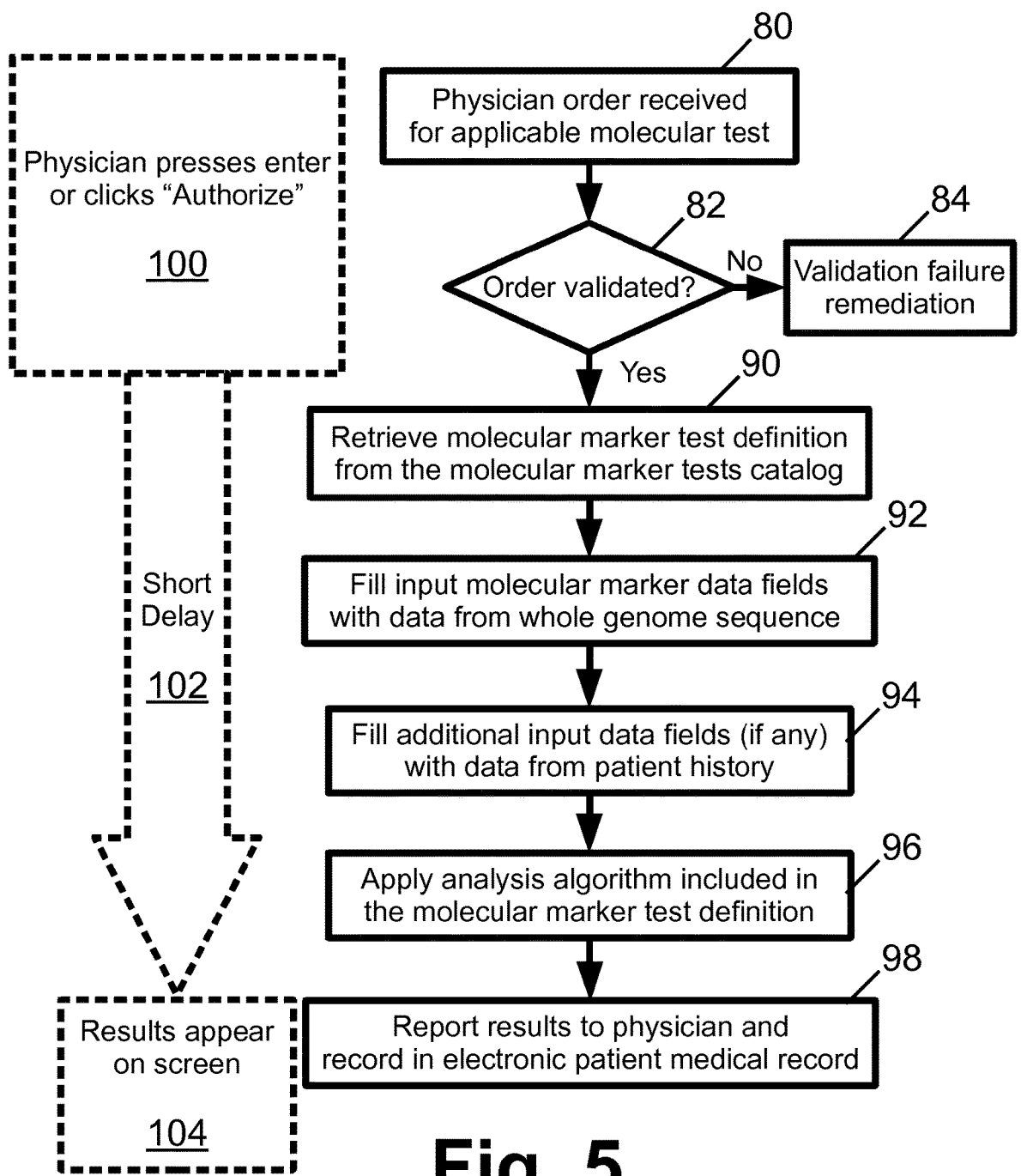

FIG. 5 diagrammatically shows performance by the system of FIG. 1 of a medical marker test identified in accordance with operations of FIG. 3.

With reference to FIG. 1, a patient 6 undergoes tissue sample extraction in a sample extraction laboratory 8. The sampling laboratory 8 extracts one or more tissue samples from the subject 6. For example, a tissue sample from the lesion may be extracted, optionally along with a normal tissue sample extracted from a location other than the lesion (and, preferably, a location into which it is not expected that the cancer has metastasized). Diagrammatic FIG. 1 shows an illustrative extracted tissue sample 10. By way of some illustrative examples, the sample 10 may comprise a biopsy sample extracted using a biopsy needle or other interventional instrument, surgical tissue sample, sputum, a hair follicle extracted by plucking, a blood drawn using a hypodermic needle, or so forth. It will be noted that in illustrative FIG. 1 the sample 10 is represented by an illustrative vial; however, it is to be understood that the sample 10 may in general take any form suitable for the type of tissue that has been sampled, and may be contained or supported by any suitable container or support for that type of tissue. For example, the sample 10 may be a fluid sample, a surface sample (e.g. obtained by oral swabs and disposed on a sterile slide or other suitable surface), or so forth. Still further, while the illustrative tissue sample 10 is represented as a single sample, it is to be understood that multiple samples may be acquired to provide material for a series of tests, and/or samples may be acquired from different areas (e.g., a suspect tissue sample from the lesion and a healthy tissue sample).

The tissue sample 10 is processed by a sequencer apparatus 14 to generate sequence fragments which are aligned and assembled by a sequence alignment/assembly module 16 (typically embodied by an illustrative computer 18 or other electronic data processing device) to generate genetic sequencing data 20 of the patient 6 that is stored in an electronic patient medical record 22 for the patient 6. In some embodiments the stored genetic sequencing data is a whole genome DNA and/or RNA sequence (WGS), although smaller portions of the genome are also contemplated. The stored genetic sequencing data also optionally includes transcriptome, methylome, Chromatin immunoprecipitation sequencing (ChIPseq), RNA immunoprecipitation sequencing (RIPseq), exome sequencing data, methylation sequencing data, or other information measured by sequencing. The genetic sequencing apparatus 14 can employ substantially any sequencer that is capable of generating a whole genome sequence (WGS). Some suitable sequencing apparatus are available from Illumina, San Diego, Calif., USA; Knome, Cambridge, Mass., USA; and Ion Torrent Inc., Guilford, Conn., USA.

In the illustrative embodiments the WGS 20 is acquired. As used herein, a "whole genome sequence", or WGS (also referred to in the art as a "full", "complete", or "entire" genome sequence), or similar phraseology is to be understood as encompassing a substantial, but not necessarily complete, genome of a subject. In the art the term "whole genome sequence" or WGS is used to refer to a nearly complete genome of the subject, such as at least 95% complete in some usages. The term "whole genome sequence" or WGS as used herein does not encompass "sequences" employed for gene-specific techniques such as single nucleotide polymorphism (SNP) genotyping, for which typically less than 0.1% of the genome is covered. The WGS 20 may include an aligned DNA sequence and/or an aligned RNA sequence, and may additionally include any unaligned DNA or RNA fragments such as are typically "left over" after the alignment and assembly processing. In general, the WGS 20 is a data file, for example in a Sequence Alignment/Map (SAM) format or a binary equivalent (e.g., BAM) format. In these formats, bases are typically represented by corresponding letters (e.g., a FASTA format) in which the bases adenine, cytosine, guanine, thymine (for DNA), and uracil (for RNA) are represented by the letters "A", "C", "G", "T", and "U", respectively. Optionally, base quality metric such as a phred quality metric may be associated with each base, as for example in the FASTQ format. The WGS 20 may optionally also include various annotations, for example delineating genetic features such as coding sequences, mutations or variants, or so forth. The foregoing are merely illustrative examples, and it is to be understood that the WGS 20 may be stored in any format suitably representing the acquired genetic sequence information.

Still further, while illustrative FIG. 1 shows a single WGS 20 for the single tissue sample 10, more generally the process may be repeated for different tissue samples, such as for a suspect tissue sample extracted from a lesion and a normal tissue sample extracted from what is believed to be healthy tissue. In this case each tissue sample is sequenced, aligned and assembled so that the WGS 20 may include (by way of example) a whole genome sequence for suspect lesion tissue and a whole genome sequence for normal tissue. In such cases, each whole genome sequence is suitably organized and labeled, e.g. as the "lesion" WGS and the "normal" WGS.

The electronic patient medical record 22 for the patient 6 optionally also stores other patient-related information besides the WGS 20, such as a patient medical history 24, medical images 26, or so forth. The electronic patient medical record 22 is typically stored in a secure medical database maintained by a hospital, clinic, or other medical facility or organization responsible for overseeing the medical treatment of the patient 6. The medical database typically resides on a computer or other electronic data processing device, such as an illustrative server 28. It is to be appreciated that the various data 20, 24, 26 may be physically located substantially anywhere (for example, the server 28 may not actually be located at the hospital but rather accessed via the Internet or another digital data network) and may be variously logically organized (for example, the medical images 26 may actually be stored in a Picture Archiving and Communications System, i.e. PACS, with the medical record 22 storing links to the images).

The acquisition and storage of the WGS 20 may in general be done at any time. If the cost of sequencing is sufficiently low, it is contemplated that the WGS acquisition be performed as a standard procedure for patients admitted to the hospital or entering certain out-patient treatment programs. Alternatively, the WGS 20 may be performed at a later point in time, for example at a point in time when the physician first orders a molecular marker test. There may also be various delays between acquisition of the tissue sample 10 at the laboratory 8, and the sample processing by the sequencer 14, and the alignment/assembly processing by the alignment/assembly component 16, 18.

The WGS 20 comprises a vast quantity of data, where different parts of the patient's genomic data are relevant at different times in the patient's progress through the care cycle. Even parts of the genome that were previously considered to be junk have been recently identified as being relevant in disease contexts, especially cancer. For example, micro-RNAs, HSATII repeats and other non-coding RNA that were previously thought to be junk have been implicated in critical cellular processes of relevance to cancer etiology, progression and likelihood of response to therapy 6. At various points during the treatment of the patient 6, it may become useful to perform a particular molecular marker test of some sort. At that point, the specific genes (or other portions) of the WGS 20 that are utilized in the particular molecular marker test to be performed are suitably extracted from the WGS 20 and used in the test. As such, the particular molecular marker test is said to be performed in silico, that is, by a computer or other electronic data processing device operating on data extracted from the WGS 20. It is to be understood that the in silico test is performed on an actual tissue sample (e.g., the sample 10 in FIG. 1), and hence is not a mere simulation. But, the tissue sample is not processed specifically to measure the genes or other genetic information used in the test, but rather is processed to extract the WGS 20. The measurements of the specific genes used in the test are then extracted from the WGS 20.

This approach potentially opens up a wide range of molecular marker testing since substantially any molecular marker test can be performed, at any time, using only a single tissue sample (or a tissue sample of each type, e.g. one lesion sample and one normal tissue sample). However, leveraging the vast quantity of data contained in the WGS 20 via in silico molecular marker testing is difficult, because as already noted very little, if any, of the data contained in the WGS 20 is probative of the patient's condition.

One approach might be to perform all available molecular marker tests using the WGS 20, store those results in the patient record, and provide a copy of the results to the treating physician. However, there are numerous difficulties with this approach. First, it would entail a large, and possibly prohibitive, amount of electronic data processing. Second, medical privacy regulations of the applicable jurisdiction may prohibit the performance of medical tests that are not specifically authorized by the patient and/or the patient's physician. Third, supplying the results of a whole catalog of molecular marker tests would likely overwhelm the physician.

Another approach might be to rely upon the physician to assess what molecular marker tests to perform, and when to order them. However, as already noted, the physician may not have up-to-date knowledge of the available tests. Also, as circumstances change a test that was not indicated when the physician made the assessment may become relevant.

With continuing reference to FIG. 1, disclosed herein is an improved approach operating in conjunction with an electronic clinical decision support (CDS) system 30. Toward this end, a context-dependent catalog search module 32 is in operative communication with the CDS system 30. For example, the search module 32 may be a plug-in that operates under control of the CDS system 30, or the search module 32 may be a wholly separate program communicating with the CDS system 30. The search module 32 compares clinical applicability annotations of molecular marker tests contained in a molecular marker tests catalog 34 with the clinical context of the patient 6 provided by the CDS system 30 in order to identify any indicated molecular marker test. The illustrative CDS system 30 employs a clinical guideline for the patient 6. The guideline is suitably selected by the treating physician from a database 36 containing clinical guideline for various medical conditions, the selection being based on the physician's initial diagnosis of the patient's condition.

In a typical embodiment, the guideline is a decision tree comprising nodes and edges or paths. The current state of the patient is represented by a node, and the edges or paths leading away from that node represent possible actions or changes in the patient's state. Typically, the guideline is designed to mimic or follow an expected treatment workflow, starting at an initial diagnosis and traversing the diagnosis stage (where the nature of the disease is determined), the prognosis stage (where the possible medical outcomes are assessed), the therapy stage (where treatment is applied in order to eliminate or mitigate the disease), and the monitoring stage (where a disease that has been eliminated or is in remission is monitored to provide early detection of any recurrence). Each of these patient care stages may be further divided; for example, the treatment stage may include a chemotherapy regimen stage and so forth. The CDS system 30 provides a convenient mechanism for assessing the past and present clinical contexts of the patient, optionally in a flowchart or other graphical format. The CDS system 30 also has an active operational aspect in which it actively guides the treating physician through the guidelines, taking into account patient-specific information. For example, the CDS system 30 may be configured to analyze the possible paths leading away from the current node and provide recommendations or other guidance to the treating physician. In some embodiments the CDS system 30 may employ a set of consensus decision rules formulated by a committee of medical experts in providing such recommendations or guidance. In some embodiments the CDS system 30 may have access to a past cases database containing past medical cases (preferably anonymized) with case outcomes, and the CDS system 30 provides guidance in the form of presenting similar cases and their outcomes from the past cases database.

With continuing reference to FIG. 1 and with further reference to FIG. 2, the guideline associated with the patient 6 and traversed by the CDS system 30 provides the clinical context for the patient 6, which is input information for searching the molecular tests catalog 34. In illustrative FIG. 2, the clinical context for each patient is a set of fields in the patient database 22 that records the procedures completed (e.g. left breast biopsy could be captured as an ICD-10-PCS code) and the current diagnosis for the patient with the relevant clinical variables entered (e.g. ER, PR and HER2 status for patient obtained from biopsy sample, could also be captured as ICD-10 codes). The context-dependent catalog search module 32 matches data in these patient database fields with the eligibility criteria provided for each biomarker in the biomarker database 34. The biomarker database can contain single or multivariate markers (signatures) that include multiple genes/loci and a decision rule for interpreting the status of the marker. In that sense, a marker is not just a piece of data (e.g. a gene name, or a gene name with a specific genomic coordinate for a location of the mutation, but a series of genomic locations with a method that is applied to the genes/genomic loci and an inferred value representing an answer to a clinical question. For example, it could be ER test when a level of the expression of the ESR1 genes is assessed based on a threshold value.

Another example is a set of 70 genes with accompanied classification algorithm that is able to provide a final prognostic assessment represented with a probabilistic value between 0 and 1 as to whether the patient needs aggressive chemotherapy or not. The patient/biomarker test matching algorithms employed by the search module 32 can be rule-based decision trees using predicate logic or probabilistic decision-making methodologies such as fuzzy logic or Bayesian inference. The output of the search module 32 is proposed patient-biomarker pairs that are likely to be useful for clinical decision-making. These matches are presented to the clinician via the physician order request/receipt module 40 for further consideration. This clinical context is also advantageously updated each time the CDS system 30 progresses the patient along the clinical guideline. Each material change in the clinical context (e.g., a change to a patient diagnostic state or procedure completion status) triggers a new search for relevant molecular marker tests. Various approaches may be used to trigger the new search. For example, the new search may be "pushed" (that is to say, triggered) by the CDS system 30, by which it is meant that the CDS system 30 invokes the catalog search module 32 to perform the search whenever the CDS system 30 updates the patient's status respective to the guideline or procedural completion. Alternatively, the new search may be "pulled" by the catalog search module 32, by which it is meant that the catalog search module 32 detects the material change in the molecular catalog and triggers the new search. 34.

In some embodiments, when the catalog search module 32 identifies a molecular marker test that is indicated by the current clinical context of the patient 6, it immediately orders the test be performed in silico using the WGS 20 of the patient 6. However, such an approach may be problematic in some jurisdictions that require specific authorization by the patient and/or the patient's physician. Accordingly, in the illustrative example of FIG. 1, a physician order request/receipt module 40 is invoked to inform the treating physician of the indicated molecular marker test and to request that the physician consider ordering this test. The physician order request/receipt module 40 optionally also provides an automated mechanism by which the treating physician can order the test. Upon receipt of an order for the test duly authorized by the treating physician, the physician order request/receipt module 40 conveys the physician order to a physician order validation sub-module 42 of an in silico molecular marker test module 44. Upon validation of the physician's order, the in silico molecular marker test module 44 retrieves the genetic data required for performing the molecular marker test from the WGS 20, performs the test using that genetic data, and generates a suitable output (e.g., a textual report directed to the treating physician and recordation in the electronic patient medical record 22.

The CDS system 30 and the processing modules 32, 40, 44 are suitably embodied by a computer 46 or other electronic data processing device such as a desktop computer, notebook computer, network server (e.g., optionally the same server 28 that embodies the database including the electronic patient medical record 22), or so forth. Although illustrative FIG. 1 shows all processing components 30, 32, 40, 44 being embodied by the single computer 46, it is alternatively contemplated to employ different computers to embody these processing components. For example, in some embodiments the CDS system 30 may be embodied by one computer and the molecular marker testing components 32, 40, 44 may be embodied by a different computer.

Further, various embodiments of processing performed by the modules 32, 40, 44 as disclosed herein may be physically embodied as a non-transitory storage medium (not shown) storing instructions executable by the electronic data processing device 46 to perform the disclosed processing. Such a non-transitory storage medium may, for example, comprise a hard disk or other magnetic storage medium, or an optical disk or other optical storage medium, or a flash memory, random access memory (RAM), read-only memory (ROM), or other electronic storage medium, or so forth.

The effectiveness of the disclosed system for pushing molecular marker tests to the treating physician is reliant upon the molecular marker tests catalog 34 being comprehensive and up-to-date with current medical research. Toward this end, the tests catalog 34 is curated by a suitably trained medical professional, or a committee or other group of trained medical professionals, using a catalog editing module 50. The human curator or curators are typically senior physicians, research scientists, or other medical personnel who are qualified to assess the quality of medical case studies, review relevant information such as regulatory decisions of the FDA or other governing regulatory agencies, and otherwise judge the advisability of including a given molecular marker test in the catalog 34. It is to be understood that the human curator or curators may have other job titles and other job duties; for example, in some contemplated settings all senior physicians having privileges at the hospital may be authorized to update the catalog 34 and hence be human curators of the catalog 34. The catalog editing module 50 can be embodied by the same computer 46 or other electronic processing device that embodies the CDS 30 and other processing components 32, 40, 44. Alternatively, as shown in FIG. 1 the catalog editing module 50 can be embodied by a different computer 52 or other different electronic data processing device that is in communication with the molecular marker tests catalog 34. For example, the computer 52 may be a dedicated workstation that is used solely for curating the catalog 34 (or, used solely for curating the catalog 34 and the CDS guidelines database 36). As another contemplated example, if there are multiple human curators then the computer 52 may be embodied as the set of desktop or other "work" computers assigned to the human curators. The catalog editing module 50 enables a human curator to add, remove, or edit molecular marker tests in the catalog 34.

In the system of FIG. 1, the molecular marker test identification components 32, 34 are not built into the clinical guideline processed by the CDS system 30, but rather are implemented as the catalog 34 which is searchable based on the clinical context indicated by the CDS system 30. Additionally, the catalog 34 is updatable using the catalog editing module 50. As a consequence, the molecular marker test identification disclosed herein is flexible, not strongly tied to the CDS clinical guidelines, and easily updated to stay current with the latest medical research. The human catalog curator does not need to understand how to edit the clinical guidelines of the CDS system 30, which can be a complex task requiring some advanced knowledge of the CDS system architecture. Additionally, when the human catalog curator updates the molecular marker test entry in the catalog 34 this update is effective for all clinical guidelines of the CDS database 36; in contrast, if the molecular marker test identification is integrated into the clinical guideline processed by the CDS system 30 then updating a single molecular marker test would entail updating each and every clinical guideline that calls for that molecular marker test.

With reference to FIG. 3, further to the foregoing the catalog 34 is preferably designed in a way that simplifies both the automated searching based on clinical context and the ease of curating. FIG. 3 diagrammatically shows the molecular marker tests catalog 34 including the fields of an entry for a single molecular marker test. These entries include: genomic data type definition; literature references annotation; disease context annotation; eligibility criteria annotation; one or more molecular marker test definitions (two test definitions are included in the illustrative entry of FIG. 3); and a results/recommendations matrix. These fields are described in turn below.

The genomic marker definition identifies the genomic markers that are analyzed. Some suitable genomic markers that may form the basis (alone or in various combinations) for a molecular marker test include: mutations; copy number variations; gene expression metrics; DNA methylation metrics; and so forth. A genomic marker may be measured in different ways. For example, consider a gene coding for a particular protein, wherein a certain mutation of that gene results in overproduction of the protein. In this case one can, in principle, measure this genomic marker by measuring the value of the gene in the DNA, or by measuring the value of the corresponding transcribed messenger RNA, or by directly measuring the expression level of the protein. The latter measurement is not available in the WGS 20, but the first two measurements are typically available in the DNA component and the RNA component of the WGS 20, respectively. The genomic marker definition identifies the genomic marker, but does not specify the measurement (e.g., DNA, RNA, or protein expression, in this case).

The literature references annotation includes citations to published studies relating to the molecular marker test, and optionally may also include citations to other relevant "literature" such as government regulatory publications pertaining to the test (if available). The physician order request/receipt module 40 optionally provides citations to these references to the physician (optionally as hyperlinks) in the proposal to perform the molecular marker test. In this way, the physician has the relevant literature handy for consultation in deciding whether or not to order the molecular marker test, and also has that literature handy to consider when evaluating the test results (assuming the physician does indeed order the test).

The disease context annotation identifies the diseases for which the molecular marker test is probative. In some embodiments, the disease context is specified by listing the International Classification of Diseases (ICD) code for each disease to which the molecular marker test applies. If the CDS system 30 uses ICD codes in identifying diseases, then performing searching of the catalog 34 respective to the disease aspect of the clinical context entails searching on ICD codes, which is fast and avoids possible ambiguities, for example if the disease in question has multiple names. Additionally or alternatively, however, the disease context may list the disease by name.

The eligibility criteria annotation specifies any additional clinical context that is relevant to the clinical applicability of the molecular marker test. Some possible eligibility criteria may include (by way of example): current patient care stage; patient age, patient gender, patient ethnicity or geographical origin, or so forth. The current patient care stage eligibility criterion annotation may be represented by the clinical guideline stage in embodiments in which the CDS system 30 employs a clinical guideline aligning with or delineating the patient care workflow. More generally, using the same patient care stage nomenclature for both the CDS system 30 and the catalog 34 enables fast and unambiguous searching respective to the current patient care stage. Eligibility criteria can also be highly disease specific. For example, eligibility criteria for the Oncotype DX® test include the patient being node negative, ER positive, and eligible for receiving tamoxifen treatment.

The one or more molecular marker test definitions define the actual molecular test in terms of the actual measurements (that is, the input molecular marker data fields) and the analysis algorithm applied to those measurements. As noted previously, different quantities can sometimes be measured to assess the same genomic marker, e.g. in the previous example one can measure the gene value in the DNA, or the gene value in the transcribed RNA, or the expression level of the translated protein. Each of these requires a different molecular marker test definition. It should also be appreciated that a given molecular marker test may utilize multiple gene measurements, e.g. the Oncotype DX® test measures 21 different molecular markers. The analysis algorithm portion of the test definition specifies the combination of these markers and the output of the combination.

In sum, each test definition defines a complete molecular marker test including the genomic coordinates of the individual loci in the marker, their actual values and the mathematical relationship between their values and the clinical outcome being queried. Again, as an example, Oncotype DX® test requires the measurement of a total of 21 genes. This marker definition suitably lists each of those genes, provide their genomics coordinates and any other information for querying the values of these genes in the WGS 20. The analysis algorithm is suitably embodied in this case by a mathematical equation that takes the measured gene expression values of the 21 genes and calculates a corresponding "recurrence score".

Although two different molecular marker test definitions are shown in the illustrative entry of FIG. 3, it is to be appreciated that there may be as few as a single molecular marker test definition provided for a given molecular marker test. On the other hand, in a molecular marker test having two or more different definitions (as in the illustrative entry shown in FIG. 3 which has two different test definitions) the different definitions are optionally ranked as to preference. In one suitable approach, the first-listed definition is the most preferred, the next-listed definition is the first alternative test if the most preferred test is unavailable (for example, because the WGS 20 does not include data filling all requisite input molecular marker data fields of the first test definition), and so on. A given molecular marker test definition may optionally include other information. For example, in illustrative FIG. 3 any certifications (e.g., FDA-approved) that have been awarded to the test definition are listed. This information may optionally be used in prioritizing the test definitions (i.e., the FDA-approved test is likely to be the most preferred, followed by alternative tests if the FDA-approved test cannot be performed). Ranking of multiple test definitions and thereby employing automatic selection from amongst the multiple test definitions is advantageous because it does not require the treating physician to decide which test definition should be used. Such a decision may be difficult for a treating physician who is not knowledgeable about the molecular marker test. However, it is alternatively contemplated to have multiple test definitions unranked, and to have the physician order request/receipt module 40 request that the treating physician identify which test definition to employ as part of the physician's order for the molecular marker test to be performed.

The result/recommendations matrix specifies the clinical conclusion or outcome of the molecular marker test. The different elements of the matrix correspond to different possible test results and the corresponding recommendations. Rather than a matrix with discrete result elements, in some cases this field may specify a computed result having a continuous dependence upon the output of the test. This field describes the clinical decision that would be impacted by the molecular marker. The result and/or recommendation may depend on the clinical context. For example, for the same test result may link to different recommendations for different clinical guideline stages as specified in the matrix.

The molecular marker test entry shown in FIG. 3 is merely an illustrative example, and it is to be understood that additional or different information may be included, and or may be in different arrangements and/or formats, in different embodiments of the catalog 34. More generally, each entry should include at least: (1) the molecular marker test definition; and (2) clinical applicability annotations for comparison with the clinical context of the patient 6. The clinical applicability annotations include at least a disease diagnosis (or diagnoses) and a current patient care stage (or stages) for which the molecular marker test has clinical applicability.

With reference to FIG. 4, context-dependent medical marker test identification as suitably performed by the system of FIG. 1 is described by way of an illustrative flow chart. In an operation 60, an event is detected that triggers a new catalog search. For example, the event may be a detected change in the clinical context tracked by the CDS system 30. As noted previously, in some embodiments such detection may be performed by the CDS system 30, while in other embodiments the detection may be performed by the catalog search module 32 via monitoring of the CDS system 30. More generally, there are various possible ways to fire a "trigger" in the system so that the matching of the patient with molecular marker tests is performed. For example, a catalog search may be triggered when guidelines are updated, or when the patient record is updated. The triggering update of the patient record could be by the physician, or could occur automatically. For example, when the patient's age changes every year, the patient may become eligible for one or more criteria of the guidelines. Consider a guideline that says for prevention and screening, a molecular marker applies only for people who are age>45, then the system should trigger a possible new test for this patient on the patient's $46^{th}$ birthday. Another way to trigger the system to perform matching of the patient with possible biomarker tests is to change or update the catalog of the molecular markers 34. As new evidence comes up for the markers, there could be one or more criteria that are contextually now applicable to the patient. Such an update may be triggered by immediate detection of the catalog update performed using the catalog editing module 50, or may be a delayed update. For example, updating the catalog may set an update flag that is checked on a regular basis, e.g. daily, so as to detect the editing of the catalog and trigger the system to perform matching of the patient with possible biomarker tests.

The automatic searching of the biomarker tests catalog 34 is suitably performed by the search module 32 responsive to any triggering event of a set of "triggers" described as rules (e.g. expressed in predicate logic, or fuzzy logic or in a probabilistic framework). For example, assume we have a patient's breast tumor sequenced, and based on the patient's clinical characteristics (age, ER/PR/HER2 status) and a biomarker test (say, OncoTypeDx), the patient was assigned to be given adjuvant chemotherapy in addition to Tamoxifen. One of the triggers that could be activated at a later point in time is the rule "patient stopped responding to treatment regime". The moment the patient's disease progressed during adjuvant therapy, the trigger would be activated and the system would search for biomarkers that could be applied to patients that have stopped responding to adjuvant therapy. If the new state of the patient makes the patient eligible for a biomarker in the database, then the physician order request/receipt module 40 will alert the physician about this possibility.

In another illustrative example, which could be in the ovarian cancer diagnostic setting, patients are regularly monitored for CA125 levels in blood. The trigger could be when a patient's CA125 level crosses a diagnostic threshold, thus making the patient now eligible for testing using new molecular markers stored in the catalog 34, using the stored genetic sequencing data stored in the electronic patient medical record 22. Meanwhile, assuming that there is a new blood-based marker for carboplatinum sensitivity, this patient can now be evaluated using the originally stored genetic sequencing data in digital format without the need for additional biopsy. In this example changes in patient state trigger the evaluation of the molecular marker tests available in the catalog 34, but the patient does not have to be biopsied again—rather, the existing digitally stored genetic sequencing data can be a surrogate for biopsies and molecular marker evaluation can be done in silico.

Other changes such as a change in clinical guidelines (for example, the new guideline could have a different patient age criterion for eligibility for adjuvant chemotherapy) would trigger a re-evaluation of all patients in the database to check if any additional patients are eligible for biomarkers that could then be evaluated for testing if the new patients would respond to chemotherapy or not. As yet another example, it could be that breast cancer patients who are on long term tamoxifen therapy could be eligible for switching to a different therapy such as letrozole or anastrozole, and this switch could be based on a molecular signature evaluation on the original biopsy. Since the full patient sequence data is available from the original biopsy, it can be queried in silico again in order to evaluate the patient's likelihood of success.

Updates of the catalog 34 of molecular marker tests can also trigger a new search. For example, if a newer biomarker has been found recently and added to the catalog 34 that has better sensitivity and specificity than an existing biomarker, this would trigger the re-evaluation of all eligible patients in the database in order to improve clinical decisions.

In an operation 62, the catalog search module 32 formulates a search query based on the clinical context of the patient 6. The clinical context may, for example, include the disease diagnosis and the current patient care stage. These typically are obtainable from the CDS system 30. For example, the CDS system 30 typically stores the disease diagnosis which is used to select the appropriate clinical guideline for the patient 6, and the current patient care stage may be suitably represented by the current clinical guideline stage for the patient. The clinical context optionally further includes other relevant information, typically obtained from the patient medical history 24, such as gender, age, current medications, or so forth. The query is formulated in a format appropriate for the storage format of the catalog 34. For example, if the catalog 34 is stored as a relational database then the query may be suitably formulated in a structured query language (SQL). If the catalog 34 is stored in a textual format then the query may be suitably formulated as a keyword search using suitable operators such as conjunctions (e.g., "AND"), disjunctions, (e.g. "OR"), negations (e.g., "NOT") or so forth. Alternatively, the search may employ a probabilistic framework. The formulation of the query is based on the automatic "triggering rules" of the system, that match the clinical context of the patient with the applicable molecular signatures. The matching could be based on first order logic resulting in binary decisions (yes/applicable or no/not applicable) or a more sophisticated Bayesian framework where soft decision rules are applied based on the thresholded probability values. (this can also have a flavor of the autonomous computing)

In an operation 66, the catalog search module 32 performs a search on the catalog 34 using the formulated search query in order to locate a molecular marker test having clinical applicability to the patient in the changed clinical context (the change having been detected in the operation 60). In a decision operation 70, the catalog search module 32 determines whether a clinically applicable test has been located. If not, then in an operation 72 the catalog search module 32 terminates the context-dependent molecular marker test search operation that was triggered by the detection operation 60.

On the other hand, if a clinically applicable molecular marker test has been located in the operation 66 as determined by the decision operation 70, then the located test is proposed to the physician. In some embodiments, an operation 74 is performed which determines whether the WGS 20 stored in the electronic patient medical record 22 contains all genetic information sufficient to perform the located molecular marker test in silico. Usually this will be the case, but there may be exceptions. For example, in some cases the WGS 20 may be incomplete and the missing portion may by happenstance contain molecular markers that are required by the test. In other cases the molecular marker test may require data that cannot be extracted from the WGS 20, such as actually measured protein expression levels. (In principle, equivalent information can usually be obtained from the DNA or RNA sequencing data contained in the WGS 20; however, in some instances there may be no test definition in the catalog 34 that defines the located molecular marker test in terms of DNA or RNA sequencing data).

In an operation 76, the physician order request/receipt module 40 proposes the located molecular marker test to the physician. This proposal may optionally include various information that may be of use to the physician in deciding whether to order the proposed test, such as: links to the relevant literature (obtained from the catalog entry); an indication of whether the test can be performed in silico (if this has been determined via optional operation 74); an indication of possible therapy modification that might be indicated based on the result of the test (useful if, for example, the physician has already decided in consultation with the patient that radiation therapy is not an option, and if the only therapy revision that the test might propose is to initiate radiation therapy); or so forth.

With reference to FIG. 5, performance by the system of FIG. 1 of a medical marker test identified in accordance with operations of FIG. 4 is described by way of an illustrative flow chart. The starting point for the flowchart of FIG. 5 is operation 76 of FIG. 4, that is, a clinically applicable molecular marker test has been located and proposed to the physician. It is also assumed in the flow chart of FIG. 5 that the stored genetic sequencing data 20 of the patient contains all molecular markers used in the proposed test, so that it can be performed in silico. From this starting point, in an operation 80 the physician order request/receipt module 40 receives an order to perform the proposed molecular marker test. (In the alternative case the physician declines to order the test and execution terminates. In another possible alternative case the physician never takes action at all. In this case the proposal may time out and execution terminates, optionally after one or more reminders are sent to the physician. These possibilities are not illustrated in FIG. 5.) Upon receipt of the physician's order it is conveyed to the order validation sub-module 42 of the in silico testing module 44 and the order validation sub-module 42 validates the order in an operation 82. The validation mechanism depends upon the format of the physician's order. For example, if an electronic signature is used then it is checked against the known electronic signature of the physician. If the physician uses a password in sending the order then the password is suitably checked. (Although not illustrated, in some embodiments the validation operation may be performed by the physician order request/receipt module 40 rather than by the testing module 44. This may be the more convenient arrangement, for example, in the case of a password check.) If the validation fails then remedial action is taken in operation 84, for example by requesting that the physician re-enter his password.

Assuming the validation is successful, the molecular marker test is carried out in silico by the molecular marker testing module 44. In an operation 90, the testing module 44 retrieves the molecular marker test definition from the catalog 34. In an operation 92 the testing module 44 accesses the WGS 20 in the electronic patient medical record 22 and fills the input molecular marker data fields of the test definition with appropriate data extracted from the WGS 20. In an operation 94, any additional input data fields (e.g., patient age, patient gender, or so forth) are filled with data obtained from the patient medical history 24 (or from another accessible source as appropriate, or by requesting the missing data be input in real time by a human operator). In an operation 96 the analysis algorithm of the test definition is applied to the data contained in the data fields that were filled in operations 92, 94, and the result is optionally used to look up treatment recommendations stored in the result/recommendations matrix of the located molecular marker test entry. In an operation 98 the results (and optional treatment recommendations) are reported to the physician.

The manifestation of the process described with reference to FIGS. 3 and 4 to the physician can be varied. Advantageously, the operations 60, 62, 66, 70, 74 are generally hidden from the physician, although in some embodiments it is contemplated to output an indication to the effect that the catalog 34 was searched and no clinically applicable test was located (for example, a notation in the electronic patient medical history 24, or in appropriate patient data stored in the CDS system 30). Typically, the first interaction with the physician is when a test is located and presented to the physician in the operation 76 of FIG. 4. In one suitable approach, this presentation is via a computer, e.g., the physician's desktop or notebook computer, or via a computer based in the patient's hospital room or at an associated nursing station, or so forth. The physician is notified of the located test, is provided with links to relevant literature, and is asked whether or not to order the located test. The physician may optionally follow the literature links (e.g., by clicking on the link using a mouse whereby the relevant literature article is displayed in a pop-up browser window or other window). If the physician chooses to order the test he or she clicks on an "ORDER TEST" button or activates some other equivalent user input (see dotted operation 100 in FIG. 5). The physician may also need to take action to validate the order, for example by inputting an electronic signature; alternatively, if the physician is logged into the computer then this logged-in status may optionally serve as validation.

An advantage of in silico testing is that it is fast. In FIG. 5 this is diagrammatically illustrated by showing an arrow 102 indicating the time interval for performing the operations 90, 92, 94, 96 comprising the in silico testing, which is terminated in an operation 104 indicating the receipt of the test results (corresponding to report operation 98). The time interval 102 depends on the complexity of the analysis algorithm applied in operation 96, the number of input parameters filled in via operations 92, 94, the processing power and load of the computer 46, and so forth. However, assuming that the identified molecular marker test is performed without delay responsive to the order receipt 80, 100, and further assuming that the test result is displayed to the physician via the computer without delay in the operation 98, 104, the time interval 102 can be reasonably expected to be reasonably short. Accordingly, the receipt 98, 104 of the test results occurs almost immediately (e.g., within a few seconds) after the order operation 80, 100. Said another way, the test is performed in real-time from the physician's viewpoint.

The flow chart of FIG. 5 assumes that the WGS 20 contains all molecular markers used in the located molecular marker test, so that the test can be performed in silico. If this is not the case, the in silico molecular marker testing module 44 is not applicable, but the context-dependent catalog search module 32 can still perform the operations shown in the flow chart of FIG. 4. In this case the operation 74 would detect that in silico testing is not possible, and the proposal operation 76 would propose the located clinically applicable molecular marker test with the additional information that a tissue sample would need to be extracted, or an already-extracted tissue sample would need to be processed, in order to perform the test. The operations 80, 82 of FIG. 5 would also be suitably performed to receive the physician's order to perform the test. However, the validated physician's order for the test would not be executed in silico but rather would be communicated to appropriate human medical personnel or an appropriate organizational entity, such as a testing laboratory, which would then acquire the necessary molecular marker data via tissue sample processing (and tissue sample extraction, if needed). Although this does not provide the advantage of real-time in silico testing, it does provide the other advantages disclosed herein, e.g. facilitating expedited adoption of new molecular marker tests, providing an updatable and automatically and actively searchable catalog of molecular marker tests that is automatically searched for relevant molecular marker tests when the clinical context of a patent changes, and so forth.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiments, the invention is now claimed to be:

1. A computer-based apparatus comprising:
   a computer readable memory configured to store a catalog of molecular marker tests, each of said molecular marker tests annotated with one or more clinical applicability annotations;

a computer readable memory configured to receive and store an electronic patient medical record comprising genetic sequencing data of a patient;

a clinical decision support (CDS) system comprising a CDS processor configured to track a clinical context of said patient wherein said clinical context includes at least a diagnosis and one or more clinical variables, and wherein said tracking comprises receiving initial and updated clinical information about the patient;

a catalog search module comprising a catalog search processor and coupled with the computer readable memory configured to store a catalog of molecular marker tests and said CDS processor, wherein the catalog search module is configured to search the catalog of molecular marker tests to identify a molecular marker test having clinical applicability to the patient in the clinical context tracked by the CDS system, and further wherein the catalog search module is automatically triggered by occurrence of a trigger event defined by a set of triggering rules, wherein the trigger event is a change in the clinical context of the patient;

an order request/receipt module comprising an order request/receipt processor coupled to said catalog search processor and configured to propose to a physician the molecular marker test identified by said catalog search module and to receive from the physician a physician order to perform said proposed molecular marker test;

a testing module comprising a testing processor coupled to said catalog search processor and configured to:
validate said physician order,
perform the molecular marker test received by said physician order in silico using the genetic sequencing data of the patient in the electronic patient medical record stored in said computer readable memory, to generate results of the molecular marker test, and
generate a report to the physician comprising the generated results of the molecular marker test; and wherein the computer readable memory configured to store the electronic patient medical record is further configured to store the results of the molecular marker test.

2. The apparatus as set forth in claim 1, wherein said set of triggering rules includes rules triggering a search responsive to a change in patient condition and rules triggering a search responsive to a change in said catalog of molecular marker tests.

3. The apparatus as set forth in claim 2, wherein the CDS processor is further configured to track the clinical context of the patient by tracking a location of the patient in a clinical guideline, said clinical guideline comprising nodes and connecting edges or paths, said molecular marker tests in the catalog are annotated with clinical applicability annotations further including clinical guideline stage applicability, and the set of triggering rules further includes rules triggering a search responsive to a change in the clinical guideline.

4. The apparatus as set forth in claim 1, further comprising:
a catalog editing module comprising an editing processor configured to enable a human curator to edit said catalog of molecular marker tests to add, remove, or edit one or more of said molecular marker tests; and
wherein said set of triggering rules further includes rules triggering a search responsive to editing of the catalog to add, remove, or edit a molecular marker test.

5. The apparatus as set forth in claim 1, wherein the catalog search processor is configured to automatically detect a change in a current patient care stage tracked by the CDS system and to automatically trigger a search of the catalog of molecular marker tests to identify a molecular marker test having clinical applicability to the patient in the clinical context tracked by the CDS system responsive to the detection of the change.

6. The apparatus as set forth in claim 1, wherein the CDS processor is configured to automatically trigger the catalog search module to search the catalog of molecular marker tests to identify a molecular marker test having clinical applicability to the patient in the clinical context tracked by the CDS system responsive to the CDS system tracking a change in a current patient care stage.

7. A method for identifying clinically relevant molecular markers in a genome of a patient, operative in conjunction with: (1) a catalog of molecular marker tests each annotated with one or more clinical applicability annotations; and (2) an electronic patient medical record comprising stored genetic sequencing data of a patient, the method comprising:
electronically tracking a clinical context of the patient using a clinical decision support (CDS) system, comprising receiving initial and updated clinical information about the patient, including at least a diagnosis and one or more clinical variables;
during the electronic tracking, automatically detecting occurrence of a trigger event defined by a set of triggering rules, wherein the trigger event is a change in the clinical context of the patient;
responsive to the detecting of a trigger event, automatically triggering an electronic search of the catalog of molecular marker tests to identify a molecular marker test having clinical applicability to the patient in the clinical context tracked by the CDS system;
proposing, to a physician, the identified molecular marker test identified by said electronic search;
receiving, from the physician a physician order to perform said proposed molecular marker test;
validating said physician order prior to performing said proposed molecular marker test in silico using said genetic sequencing data of the patient;
performing the identified molecular marker test in silico using the stored genetic sequencing data of the patient, to generate results of the identified molecular marker test;
reporting the results of the identified molecular marker test to the physician; and
storing the result of the identified molecular marker test in the electronic patient medical record.

8. The method as set forth in claim 7, wherein the set of triggering rules includes:
rules triggering an electronic search of the catalog of molecular marker tests responsive to a change in a clinical guideline used by the CDS system;
rules triggering an electronic search of the catalog of molecular marker tests responsive to a change in patient record data, and
rules triggering an electronic search of the catalog of molecular marker tests responsive to an update of the catalog of molecular marker tests.

9. The method as set forth in claim 7, wherein the electronic searching employs search parameters defining a clinical context of the patient including at least a disease diagnosis and a current patient care stage.

10. The method as set forth in claim 7, further comprising:
acquiring genetic sequencing data comprising a whole genome sequence of the patient; and
storing the whole genome sequence in an electronic patient medical record that also stores an electronic medical history of the patient.

11. The method as set forth in claim 7, further comprising:
receiving a catalog update comprising addition, modification, or removal of a molecular marker test via a user interface device; and
updating the catalog with the received catalog update;
wherein the updating does not modify any clinical guideline used by the CDS system.

12. A non-transitory storage medium storing instructions executable by an electronic processing device to perform a method of identifying clinically relevant molecular markers in a genome of a patient, operative in conjunction with a catalog of molecular marker tests specifying molecular marker tests annotated with clinical applicability annotations and stored genetic sequencing data of a patient, the method comprising:
electronically tracking a clinical context of the patient using a clinical decision support (CDS) system, comprising receiving initial and updated clinical information about the patient, including at least a diagnosis and one or more clinical variables;
during the electronic tracking, automatically detecting occurrence of a trigger event defined by a set of triggering rules, wherein the trigger event is a change in the clinical context of the patient;
responsive to the detecting of a trigger event, automatically triggering an electronic search of the catalog of molecular marker tests to identify a molecular marker test having clinical applicability to the patient in the clinical context tracked by the CDS system; and
proposing, to a physician, the molecular marker test identified by said electronic search;
receiving, from the physician a physician order to perform said proposed molecular marker test;
validating said physician order prior to performing said proposed molecular marker test in silico using said genetic sequencing data of the patient;
performing the identified molecular marker test in silico using the stored genetic sequencing data of the patient, to generate results of the identified molecular marker test;
reporting the results of the identified molecular marker test to the physician; and
storing the results of the identified molecular marker test in an electronic patient medical record.

* * * * *